United States Patent
Haarer

(10) Patent No.: US 9,757,541 B2
(45) Date of Patent: Sep. 12, 2017

(54) DILATOR SYSTEMS AND METHODS

(71) Applicant: W. L. Gore & Associates, Inc., Newark, DE (US)

(72) Inventor: Joshua C. Haarer, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 0 days.

(21) Appl. No.: 14/851,358

(22) Filed: Sep. 11, 2015

(65) Prior Publication Data

US 2016/0001045 A1    Jan. 7, 2016

Related U.S. Application Data

(63) Continuation of application No. PCT/US2014/056511, filed on Sep. 19, 2014.

(60) Provisional application No. 61/880,020, filed on Sep. 19, 2013.

(51) Int. Cl.
| | | |
|---|---|---|
| *A61M 25/01* | (2006.01) | |
| *A61M 25/06* | (2006.01) | |
| *A61M 25/09* | (2006.01) | |
| *A61M 29/00* | (2006.01) | |

(52) U.S. Cl.
CPC .. *A61M 25/0662* (2013.01); *A61M 25/09041* (2013.01); *A61M 29/00* (2013.01); *A61M 2025/0681* (2013.01)

(58) Field of Classification Search
CPC .......... A61M 25/0662; A61M 25/0041; A61M 2025/0681; A61M 29/00; A61M 25/0053; A61M 25/0054; A61M 2210/125

USPC ...................... 604/164.1, 264, 510, 523, 532
See application file for complete search history.

(56) References Cited

U.S. PATENT DOCUMENTS

| | | | |
|---|---|---|---|
| 4,917,102 A | 4/1990 | Miller et al. | |
| 5,445,625 A * | 8/1995 | Voda .................. | A61M 25/0041 604/523 |
| 6,152,912 A | 11/2000 | Jansen et al. | |
| 6,185,449 B1 * | 2/2001 | Berg .................. | A61M 25/0662 600/435 |
| 6,595,959 B1 | 7/2003 | Stratienko | |
| 6,650,923 B1 * | 11/2003 | Lesh .................... | A61B 5/0084 600/332 |
| 6,926,728 B2 | 8/2005 | Zucherman et al. | |
| 7,056,294 B2 * | 6/2006 | Khairkhahan ... | A61B 17/32037 600/435 |

(Continued)

FOREIGN PATENT DOCUMENTS

| | | |
|---|---|---|
| EP | 2 133 115 | 12/2009 |
| WO | 01/70321 | 9/2001 |

(Continued)

OTHER PUBLICATIONS

International Search Report and Written Opinion for PCT/US2014/056511 mailed May 7, 2015, 8 pages.

*Primary Examiner* — Gerald Landry, II

(57) ABSTRACT

Embodiments relate to a dilator and catheter introducer systems. The dilator system includes a dilator including a dilator lumen, and one or more cores for positioning in the dilator lumen. The catheter introducer systems further include a sheath including a sheath lumen operable to receive at least a portion of the dilator therein. Each core imparts a curvature to the dilator; modify the bending resistance of the dilator, or a combination thereof.

84 Claims, 16 Drawing Sheets

(56) References Cited

U.S. PATENT DOCUMENTS

| | | | |
|---|---|---|---|
| 8,012,143 B1* | 9/2011 | Kampa | A61M 25/0041 604/264 |
| 2003/0093060 A1 | 5/2003 | Kempf | |
| 2003/0208220 A1* | 11/2003 | Worley | A61M 25/0041 606/190 |
| 2004/0092867 A1 | 5/2004 | Murray | |
| 2004/0215139 A1* | 10/2004 | Cohen | A61N 1/056 604/95.04 |
| 2005/0021003 A1* | 1/2005 | Caso | A61M 25/0152 604/528 |
| 2005/0131450 A1* | 6/2005 | Nicholson | A61B 17/221 606/200 |
| 2005/0143689 A1 | 6/2005 | Ramsey | |
| 2006/0074398 A1* | 4/2006 | Whiting | A61M 25/0041 604/510 |
| 2006/0155302 A1 | 7/2006 | Sisken et al. | |
| 2007/0299404 A1* | 12/2007 | Katoh | A61M 25/008 604/173 |
| 2008/0208166 A1* | 8/2008 | Goode | A61M 25/0662 604/510 |
| 2008/0243222 A1* | 10/2008 | Schafersman | A61M 25/0662 623/1.11 |
| 2008/0306468 A1* | 12/2008 | Tamai | A61M 25/09 604/528 |
| 2009/0281498 A1 | 11/2009 | Acosta et al. | |
| 2009/0312786 A1* | 12/2009 | Trask | A61M 25/0606 606/192 |
| 2012/0109079 A1* | 5/2012 | Asleson | A61B 17/00234 604/272 |
| 2012/0310212 A1 | 12/2012 | Fischell et al. | |
| 2014/0025041 A1* | 1/2014 | Fukuoka | A61M 25/0041 604/523 |

FOREIGN PATENT DOCUMENTS

| | | |
|---|---|---|
| WO | 03/106511 | 12/2003 |
| WO | 2009/045276 | 4/2009 |

* cited by examiner

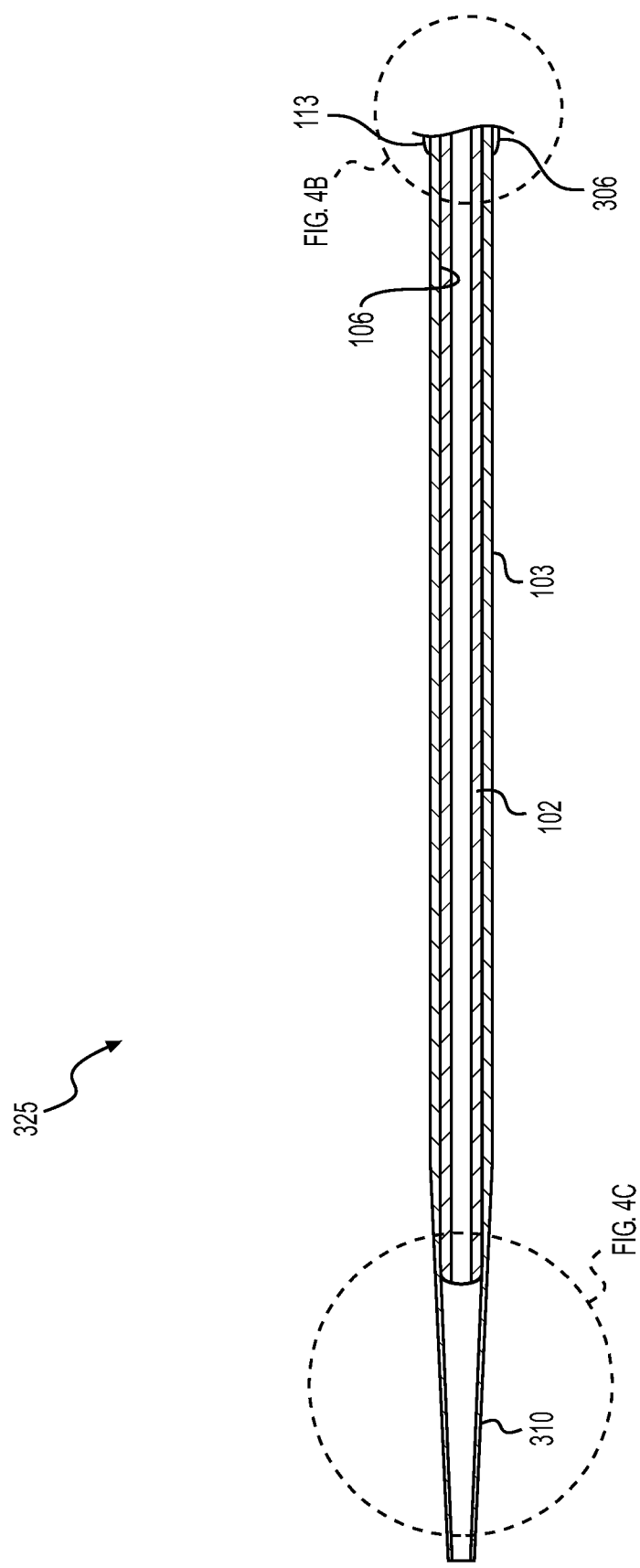

DILATOR SYSTEMS AND METHODS

FIELD

This disclosure relates to dilator systems and methods. More particularly, the disclosure relates to dilator and catheter introducer systems and methods for traversing tortuous blood vessels.

BACKGROUND

Catheter introducer systems are often introduced into blood vessels and organs for intraluminal diagnostics, treatment and delivery of medical devices and structures. The type of catheter introducer system utilized depends on the medical procedure performed, the route in the body taken, and individual patient anatomy, among other factors. A tortuous blood vessel refers to a blood vessel that is particularly difficult to advance an intraluminal device through, such as a catheter introducer system, usually due to tight and/or reverse bends defined by the path of the blood vessel. An example of a procedure that traverses particularly tortuous blood vessels is where transvenous access to the main pulmonary artery is desired from the femoral vein.

Dilators are used to expand narrowed blood vessels and/or to enable the introduction of a larger diameter intraluminal device. Dilators are limited in their ability to navigate tortuous bends. Where a guidewire may be able to traverse a particular bend, a dilator and sheath system may not be able to track over the guidewire and traverse the particular bend. Prior art dilator and sheath systems are designed to be advanced as a single unit. This method of operation, combined with dilators not substantially longer than their associated sheath, results in an abrupt transition in bending stiffness from the guidewire to the dilator and sheath system. The guidewire may be deflected out of position by the dilator and sheath instead of the guidewire presenting itself as a stable track path. Further, the tip of the sheath may abut and damage the blood vessel. What is needed in the art is a dilator system capable of traversing tortuous blood vessels, and a catheter introducer system including the dilator system that is capable of traversing tortuous blood vessels.

SUMMARY

Embodiments relate to a dilator system for accessing a blood vessel. The dilator system includes a dilator and core. The dilator is an elongated tubular member defining a dilator lumen. The core is an elongated member operable for positioning in the dilator lumen to impart a curvature to the dilator, modify the bending resistance of the dilator, or a combination thereof.

Embodiments relate to a catheter introducer system for accessing a blood vessel. The catheter introducer system includes a dilator, a core, and a sheath. The dilator is an elongated tubular member defining a dilator lumen. The core is an elongated member operable for positioning in the dilator lumen to impart a curvature to the dilator, modify the bending resistance of the dilator, or a combination thereof. The sheath is an elongated tubular member including a sheath proximal end and a sheath distal end opposite from the sheath proximal end. The sheath defines a sheath lumen extending from the sheath proximal end to the sheath distal end therethrough. The sheath lumen is operable to slidingly receive the dilator therein and to allow the sheath to advance over the dilator. The sheath is operable to track over the curvature of the dilator as imparted by the core.

Embodiments relate to a catheter introducer guidewire system for accessing a blood vessel. The catheter introducer guidewire system comprises the catheter introducer system above and a guidewire. The core is an elongated member defining a core lumen. The core lumen is operable to receive the guidewire therethrough and the core is operable to be advanced over the guidewire.

Embodiments relate to a dilator guidewire system for accessing a blood vessel. The dilator guidewire system comprises the dilator system above and a guidewire. The core is an elongated member defining a core lumen. The core lumen is operable to receive the guidewire therethrough and the core is operable to be advanced over the guidewire.

Embodiments relate to a sheath for a catheter introducer system. The sheath is an elongated tubular member including a sheath proximal end and a sheath distal end opposite from the sheath proximal end. The sheath defines a sheath lumen extending from the sheath proximal end to the sheath distal end therethrough. The sheath includes one or more regions of varied stiffness. The sheath includes a sheath distal tip positioned at the distal end of the sheath. The sheath distal tip is more stiff than an adjacent region of varied stiffness.

Embodiments also relate to methods of positioning a catheter introducer system in a blood vessel.

BRIEF DESCRIPTION OF THE DRAWINGS

The accompanying drawings are included to provide a further understanding of the present disclosure and are incorporated in and constitute a part of this specification, illustrate embodiments described herein, and together with the description serve to explain the principles discussed in this disclosure.

FIG. 4A is a side cross-sectional view of a distal region of a catheter introducer system, in accordance with an embodiment;

DETAILED DESCRIPTION

Figure 1:
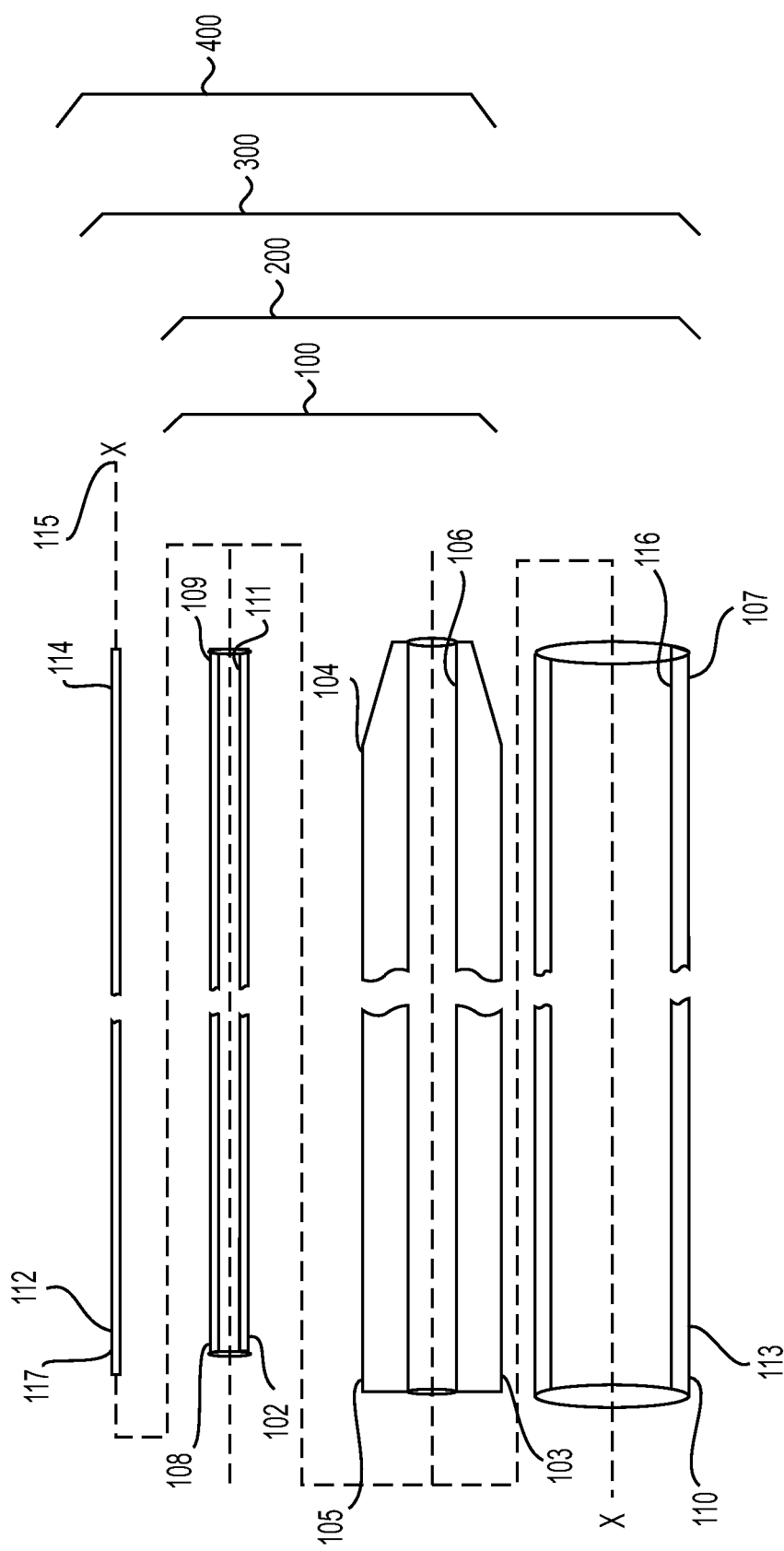
FIG. 1 is a cross-sectional view of systems in accordance with embodiments.

Persons skilled in the art will readily appreciate that various aspects of the present disclosure can be realized by any number of methods and apparatus configured to perform the intended functions. Stated differently, other methods and apparatuses can be incorporated herein to perform the intended functions. It should also be noted that the accompanying drawing figures referred to herein are not necessarily drawn to scale, but may be exaggerated to illustrate various aspects of the present disclosure, and in that regard, the drawing figures should not be construed as limiting.

Embodiments provided herein relate to dilators and catheter introducer systems that allow transvenous access to the main pulmonary artery from the femoral vein but can be applied in any situation involving access through tortuous blood vessels. Embodiments of a dilator system include a dilator and one or more cores that are operable to impart a predetermined curve to the dilator. Embodiments utilize one or more cores that are operable to be inserted within a dilator lumen of the dilator to alter or impart one or more curves in a dilator distal end.

Further, embodiments of a catheter introducer system are provided that include a dilator and one or more cores that are operable to impart a predetermined curve to the dilator over which a sheath of a catheter introducer system may traverse.

Further, embodiments of a sheath of a catheter introducer system are provided comprising a relatively more stiff sheath distal tip as compared with the rest of the sheath distal end. A more stiff sheath distal tip reduces ovalization of the sheath distal tip as the sheath distal tip traverses a curve induced by a core so as to prevent damage to the blood vessel.

As used herein, "blood vessel" refers to not only an element of the vasculature, but any blood conduit of the cardiovascular system, including the heart.

As used herein, a "tortuous" blood vessel refers to a blood vessel that is particularly difficult to advance an intraluminal device through usually due to tight and/or reverse bends defined by the path of the blood vessel. An example of a procedure that traverses particularly tortuous blood vessels is where transvenous access to the main pulmonary artery is desired from the femoral vein.

As used herein, "dilator" refers to an elongated tubular member that may be used to enlarge or stretch a body part, such as a blood vessel, cavity, canal, or orifice. A dilator may be used to introduce and guide a sheath into and through a blood vessel. A dilator is relatively less stiff than a sheath in accordance with constructs presented therein.

As used herein, "lumen" refers to a longitudinal cavity or through-bore along the longitudinal axis in a tubular component. A lumen may extend partially, completely or substantially the axial length of a component, such as a dilator, sheath or core, for example.

As used herein, "assembly" or "introducer assembly" refers to two or more components of a catheter introducer system, such as combinations of dilators, sheaths, guide wires and cores.

As used herein, "shaped" refers to a component formed to a predetermined pattern, geometry, curvature or angle. Cores or dilators may be shaped such as to conform to or follow a particular form or pattern. Cores or dilators may include curves in one or more planes and/or in three-dimensional configurations. Cores may also be straight and used only to impart a desired level of stiffness to the system.

As used herein, "core" refers to an elongated tubular member capable of being received within a dilator lumen so as to impart a desired shape and/or stiffness to the dilator. The core can be manufactured of any material possible of forming and supporting a curve, such as, but not limited to, a metal, thermoplastic or molded or cast thermoset material.

Nylon is an example of a material that may be used to form a core. Stainless steel and nitinol are examples of metals that may be used to form a core.

As used herein, "sheath" refers to a relatively more stiff, relative to a dilator, elongated tubular member operable for providing a guide way or conduit for introducing medical devices such as catheters into the body. A system utilizing a sheath advanced over a dilator is often used. The sheath may be positioned within the body with the assistance of a dilator.

As used herein, "curve" and "curvature" refer to a shape, geometry or radius of a component, such as a core or dilator. The curve of a component may be formed in one or more planes or in three-dimensional configurations and each component (e.g., dilator or core) can include none (straight), one, or more than one curve.

As used herein, "bend" refers to a change of direction of the path defined by a blood vessel, organ or other body cavity.

As used herein, "stiffness" refers to the property of a component to resist bending. A core may be used to provide a system with increased stiffness as compared with the stiffness of the individual components making up the system. For example, advancing a relatively stiff core within a dilator lumen of a relatively less stiff dilator will provide a core/dilator assembly with a higher stiffness than the dilator itself.

As used herein, "guidewire" refers to a wire or small diameter elongated member that may be advanced through a blood vessel or cavity of the body.

As used herein, "distal" refers to a region or location positioned away from a point of origin or attachment.

As used herein, "proximal" refers to a region or location positioned adjacent or near a point of origin or attachment.

As used herein, "tapered" refers to a change in physical dimension along a length of a component.

As used herein, "elongated" refers to a region of extended length.

As used herein, "radiopaque marker" refers to an element that resists the passage of x-ray or other electromagnetic radiation for at least the purpose of monitoring positioning using x-ray techniques.

As used herein, "interchangeably" refers to two or more components that can replace one another in a similar position or function. For example, two or more cores may be interchangeable within a dilator to impart differing curves onto the dilator.

FIG. 1 shows an exploded cross-sectional view of various systems all of which comprise a dilator 103 and a core 102, and with or without additional components such as a guidewire 112 and a sheath 113, in accordance with various embodiments. In the embodiments provided herein, the dilator 103 and core 102 may be provided and used together as a dilator system 100. The dilator 103 and core 102 may also be a part of a larger system and used to facilitate the use of a sheath 113 which may or may not be supplied as part of the dilator system 100 comprising the dilator 103 and core 102. Also, a guidewire 112 may or may not be provided and used as part of the system. Various combinations of systems comprising the dilator 103 and the core 102 as common components are provided below.

FIG. 1 shows an exploded cross-sectional view of a dilator system 100 comprising a core 102 and a dilator 103, in accordance with an embodiment. The core 102 is an elongated tubular member that is operable to be advanced within the dilator 103 as will be detailed below. The dilator 103 is an elongated tubular member that is operable to accept the core 102 therein and to allow the core 102 to advance at least partially within the dilator 103. As will be provided below, one or more cores 102 having different characteristics may be provided in accordance with embodiments which are operable to impart characteristics to the dilator 103.

FIG. 1 also shows an exploded cross-sectional view of a catheter introducer system 200 comprising the dilator system 100 and a sheath 113, in accordance with an embodiment. The sheath 113 is an elongated tubular member having a sheath proximal end 110 and a sheath distal end 107 opposite from the sheath proximal end 110. The sheath 113 further includes a sheath lumen 116 extending from the sheath proximal end 110 to the sheath distal end 107, therethrough. The sheath lumen 116 defines a diameter that is operable to slidingly receive the dilator 103 therein and to allow the sheath 113 to advance over the dilator 103.

FIG. 1 also shows an exploded cross-sectional view of a catheter introducer guidewire system 300 comprising the catheter introducer system 200, and a guidewire 112, in accordance with an embodiment. The guidewire 112 is an elongated member that is operable for traversing tortuous blood vessels. Guidewires are well known in the art. The core 102 including the core lumen 111 is operable to be advanced over the guidewire 112 as will be detailed below. Also, the dilator 103 including the dilator lumen 106 is operable to be advanced over the guidewire 112 as will be detailed below.

FIG. 1 also shows an exploded cross-sectional view of a dilator guidewire system 400 comprising the dilator system 100 and a guidewire 112, in accordance with an embodiment. The core 102 including the core lumen 111 is operable to be advanced over the guidewire 112 as will be detailed below. Also, the dilator 103 including the dilator lumen 106 is operable to be advanced over the guidewire 112 as will be detailed below.

Dilator System

The dilator system 100 will be discussed below. The dilator system 100 comprises a core 102 and a dilator 103, in accordance with the embodiment of FIG. 1. The core 102 is used in cooperative engagement with the dilator 103 to assist the passage of the dilator 103 through bends of a blood vessel.

The dilator 103 is an elongated tubular member having a dilator proximal end 105 and a dilator distal end 104 opposite from the dilator proximal end 105. The dilator 103 further includes a dilator lumen 106 extending from the dilator proximal end 105 to the dilator distal end 104, therethrough. The dilator lumen 106 defines a diameter that is operable to slidingly receive the core 102 therein and allow the core 102 to be advanced at least partially within the dilator lumen 106.

By way of example, in accordance with an embodiment, the dilator 103 includes a dilator lumen 106 with a diameter of about 0.5 mm to about 4 mm, about 2 mm to about 3 mm or about 2.5 mm to about 2.90 mm.

The dilator 103 may be manufactured of any suitable material for the particular purpose, such as, but not limited to, a thermoplastic. The dilator 103 comprises a material property with sufficient stiffness to enlarge the blood vessel but not so stiff to damage the blood vessel or not be able to be guided within bends of the blood vessel by the core 102.

Figure 3:
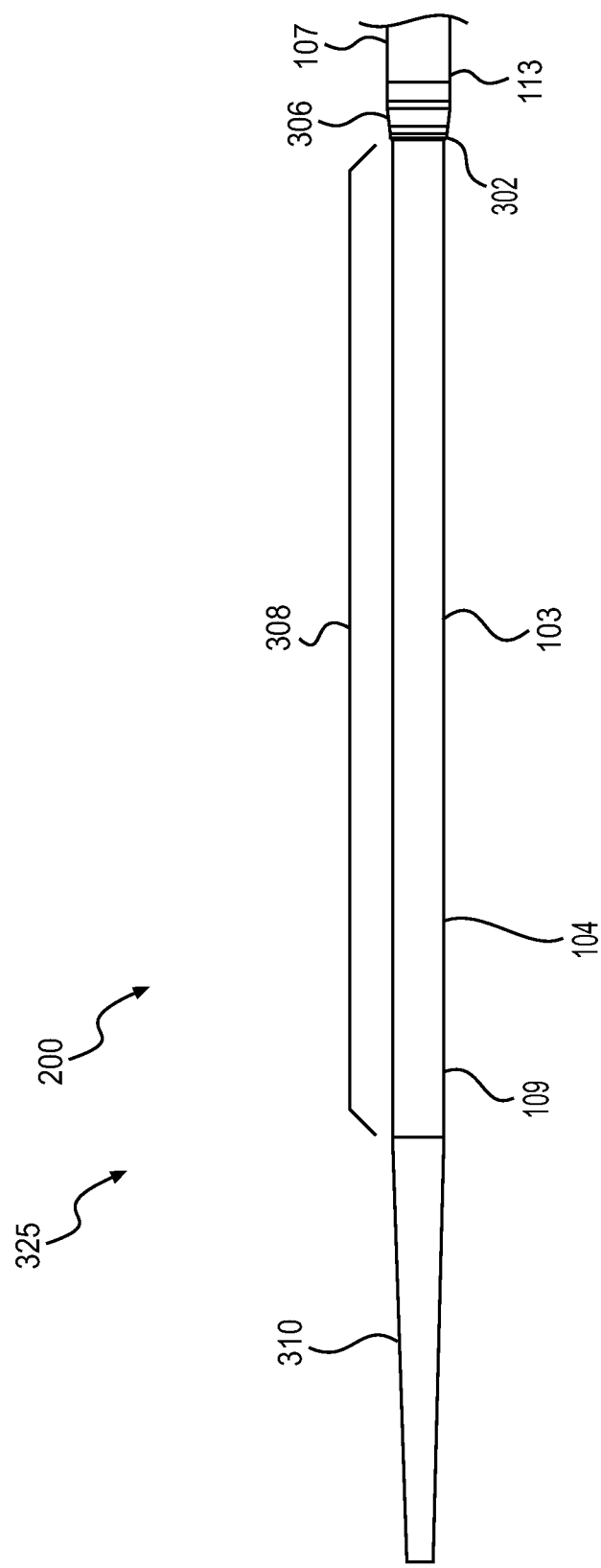
FIG. 3 is a side view of a distal region of a catheter introducer system, in accordance with an embodiment.
Figure 4B:
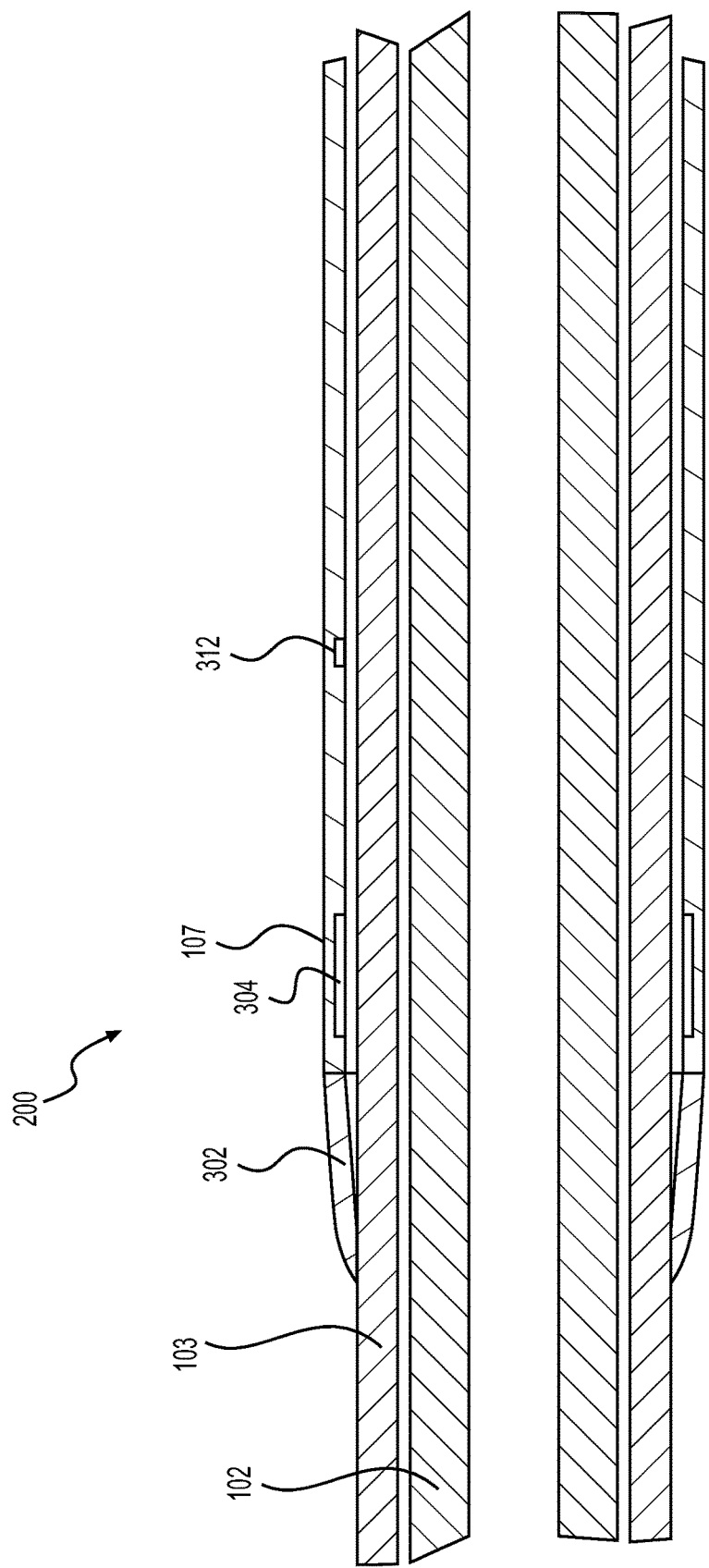
FIG. 4B is an enlarged side cross-sectional view of the dilator sheath interface of a catheter introducer system of FIG. 4A.
Figure 4C:
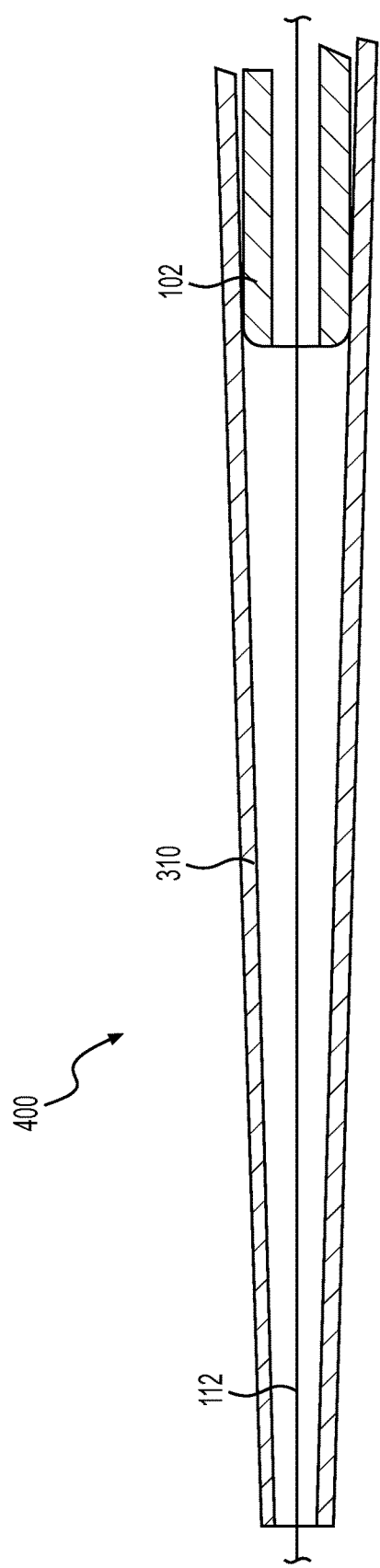
FIG. 4C is an enlarged side cross-sectional view of a dilator tip of a catheter introducer system of FIG. 4A.

Referring to FIG. 3, which shows a side view of the dilator 103, the dilator distal end 104 may include a dilator distal tip 310. The dilator distal tip 310 may be an integral element of the dilator distal end 104 or an element that is coupled to the dilator distal end 104. The dilator distal tip 310 may be tapered. In accordance with an embodiment, the dilator distal tip 310 defines a dilator tip lumen comprising a diameter that is less than a diameter of the core 102 whereby preventing the core 102 from extending beyond the dilator distal tip 310. The lumen of the dilator distal tip 310 may also be tapered to a smaller diameter than the diameter of the core 102, as shown in FIGS. 4A and 4C, such that the core may not exit the dilator distal tip 310, thus preventing the core 102 from injuring the blood vessel.

A dilator 103 may be formed by any suitable process, such as, but not limited to extrusion. The dilator distal tip 310 may be formed by any suitable process, such as, but not limited to, injection molding. The dilator distal tip 310 and dilator distal end 104 may be joined by any suitable process, such as, but not limited to thermal and chemical bonding. A dilator distal tip 310 that is coupled to the dilator distal end 104 may facilitate the production of a dilator distal tip 310 with a lumen that is tapered to a smaller diameter than the diameter of the core 102, as shown in FIGS. 4A and 4C. The dilator distal tip 310 may also be formed on the dilator distal end 104 as a one-piece component by any suitable process, such as, but not limited to, grinding.

In accordance with embodiments, the dilator distal tip 310 has a length of about 1 cm to about 10 cm, about 3 cm to about 8 cm or about 4 cm to about 7 cm. The dilator distal tip 310 may be elongated to allow for greater adaptability with the core 102 and work in conjunction with the elongated dilator distal region 308, as will be discussed below. The dilator distal tip 310 may or may not be tapered, but in most embodiments, a taper is provided on the outer diameter of the dilator distal tip 312 so that the blood vessel 203 is not exposed to steps and edges, and the lumen of the dilator distal tip 310 is tapered to a smaller diameter than the outer diameter of the core 102 thus preventing the core 102 from extending beyond the dilator distal tip 310 and possibly injuring the blood vessel.

The dilator 103 may include a radiopaque marker, such as, but not limited to an element that is coupled to the dilator 103 or by integrating doping materials into the construct, such as, but not limited to, barium sulfate.

Referring again to FIG. 1, the core 102 is an elongated tubular member having a core proximal end 108 and a core distal end 109 opposite from the core proximal end 108. The core 102 further includes a core lumen 111 extending from the core proximal end 108 to the core distal end 109, therethrough. The core lumen 111 defines a diameter that is operable to slidingly receive a guidewire 112 therein and to allow the core 102 to advance over the guidewire 112. The core 102 defines an outer diameter operable to be slidingly received within the dilator lumen 106 and to allow the core 102 to advance at least partially within the dilator lumen 106.

Although the core 102 is shown as an elongated tubular member including a core lumen 111, it is appreciated that for systems and uses that do not involve a guidewire 112 or other need for a lumen, such as, but not limited to irrigation, the core 102 may be an elongated member not having a lumen therethrough. In the discussion of the embodiments provided below, the core 102 will comprise a core lumen 111, but will not be limited thereto. It is appreciated that for most uses, a guidewire 112 will be used with or as part of the system including a dilator 103 and core 102. By way of example, in accordance with an embodiment, the core lumen 111 may have a diameter of about 0.38 mm to about 1.3 mm.

Figure 2A:
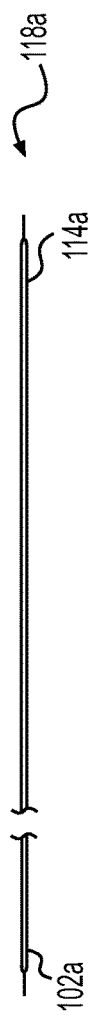
FIGS. 2A-E are side views of cores, in accordance with various embodiments.
Figure 2B:
Figure 2C:
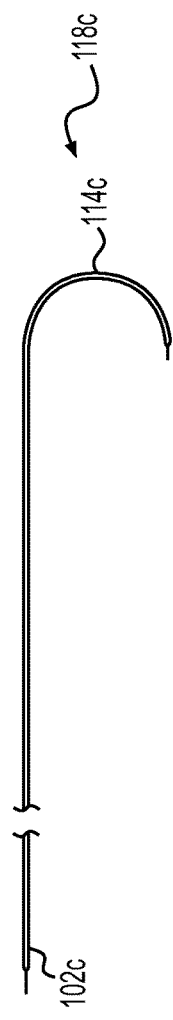
Figure 2D:
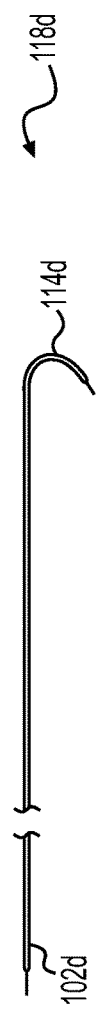
Figure 2E:
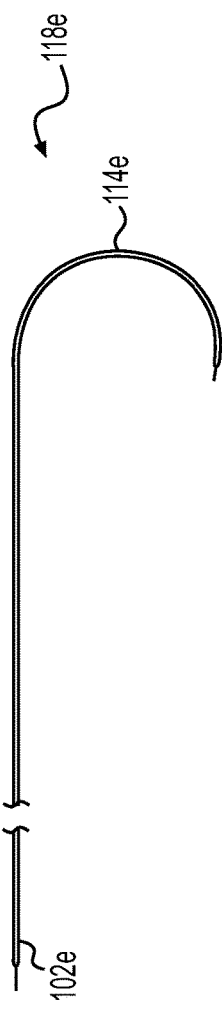

FIGS. 2A-5E are side views of five cores 102*a-e* each having a core distal end 109*a-e* defining a different core curve 118*a-e*. FIG. 2A shows a first core 102*a* having a distal end 114*a* defining a core curve 118*a* that is straight. The first core 102*a* may be used to support the dilator 103 in a substantially straight configuration and/or to impart a stiffness to the dilator 103 that may assist in advancing the dilator 103 through the blood vessel.

FIGS. 2B-E are side views of a second, third, fourth and fifth core 102*b-e* each having core distal ends 114*b-e* defining different core curves 118*b-e*. The core curves 118*b-e* may be planar or in a three-dimensional configuration. The core curves 118*b-e* may define a radius of curvature, such as, but not limited to, from about 5 mm to about 100 mm. In accordance with embodiments, each core 102 may include multiple core curves 118 with one or more radii of curvature. It is appreciated that the core curves 118 may define any shape suitable for the particular purpose of supporting a dilator 103 to track a bend in a blood vessel. The core curves 118 may not define a constant radius and may be compound curves of various radii on different planes.

The core 102 may be manufactured of any suitable material for the particular purpose, such as, but not limited to, a thermoplastic and metal, such as, but not limited to, stainless steel and nickel titanium alloy. The core curve 118 in the cores 102 may be formed by any suitable process for a particular material, such as, but not limited to, thermal shape-setting and molding.

In accordance with an embodiment, the core 102 may be of the type that is steerable, such as by utilizing active steering mechanisms that are known in the art for steering catheters.

In accordance with an embodiment, one or more radiopaque markers may be coupled to or integrated with the core 102. The radiopaque markers may be positioned near or on the core distal end 109 so as to identify a location of the core distal end 109 when imaged by x-ray techniques, for example.

The dilator 103 is operable to dilate (enlarge) narrow portions of a blood vessel for the purpose of, for example, but not limited to, ensuring that the blood vessel may accept a catheter or sheath therein. In operation, in accordance with an embodiment, the dilator distal end 104 is advanced through the blood vessel. At narrow portions of the blood vessel, the dilator 103 comes into urging engagement with and enlarges the diameter of the blood vessel.

At locations where the blood vessel presents a bend, the dilator distal end 104 may mistrack, that is, not follow the path of the bend. To assist the dilator distal end 104 to track the bend, a core 102 is inserted into the dilator lumen 106 at the dilator proximal end 105 and is advanced to the dilator distal end 104 at that location where the dilator 103 may tend to mistrack. The core distal end 109 is provided with a predetermined curve that is operable to impart a curve to the dilator distal end 104 suitable to direct the dilator distal end 104 through the bend of the blood vessel. The core 102 need not extend beyond the dilator distal end 104. The relative stiffness of the core 102, which is greater than the stiffness of the dilator 103, tends to urge or direct the dilator distal end 104 towards and into the bend about the curve imposed by the core distal end 109. Once the dilator distal end 104 is beyond the bend, the core curve 118 defined by the core distal end 109 is placed within the bend. The core 102 may be held in place while the dilator 103 is advanced over the core 102 and through the bend with the core 102 guiding the dilator 103.

In many cases, the procedure of enlarging a blood vessel will entail the use of one core 102 having a particular core curve 118 at the core distal end 109. In other cases, the dilator 103 may be advanced to a subsequent bend in the blood vessel that does not have the same bend as the previous bend. The dilator system 100 provides that the core 102 may be removed from the dilator 103 and a subsequent core 102 having a different core curve 118 may be advanced into and with the dilator 103 to the subsequent bend, with the above method repeated to allow the dilator distal end 104 to pass through the subsequent bend.

The dilator distal end 104 defines a taper of diminishing outer diameter that terminates at a dilator distal tip 310, as shown in FIGS. 3 and 4A, where FIG. 4A shows a cross-sectional view of the dilator 103. The taper allows for, among other things, the dilator distal end 104 to have a reduced relative stiffness as compared with the non-tapered portion of the dilator distal end 104. Although the non-tapered portion of the dilator 103 has a relative stiffness that is less than that of the core 102, the core curve 118 defined by the core distal end 109 will be substantially straightened when inserted into the dilator lumen 106 within the non-tapered portion of the dilator 103 when the dilator 103 is supported by a blood vessel, or in an embodiment with a sheath, the dilator 103 is supported by the sheath, as will be discussed below.

The lumen of the dilator distal tip 310 is also tapered to a smaller diameter than the diameter of the core 102, as shown in FIGS. 4A and 4C, such that the core may not exit the dilator distal tip 310, thus preventing the core 102 from extending beyond the dilator distal tip 310 and possibly injuring the blood vessel. In accordance with an embodiment, the dilator distal tip 310 defines a dilator tip lumen comprising a diameter that is less than a diameter of the core 102 whereby preventing the core 102 from extending beyond the dilator distal tip 310.

When the dilator distal end 104 and core 102 are advanced into a bend as an assembly, that is, the core 102 is within the dilator distal end 104, the dilator distal end 104 is no longer supported by the blood vessel and has insufficient stiffness and exterior support to retain the core distal end 109 in a substantially straightened configuration and therefore the core distal end 109 will impart a curve to the dilator distal end 104. The dilator distal tip 310 may then be directed into the bend of the blood vessel. Once the dilator distal tip 310 traverses the bend, the core 102 may be held in place with the core curve 118 of the core 102 imparting a curve to the dilator 103 that substantially corresponds to the bend of the blood vessel, as the dilator 103 is advanced over the core 102 and through the bend.

A number of cores 102 defining various predetermined core curves 118 may be provided operable to impose a curve to the dilator 103 suitable to allow the dilator 103 to traverse a bend of the blood vessel, in accordance with embodiments. A dilator system 100 may comprise one core 102 that is operable to be shaped to a particular core curve 118 by a user, in accordance with an embodiment. The dilator system 100 may comprise one of a number of cores 102, each core 102 defining a different core curve 118 or core curves 118 that a user may select prior to a procedure, in accordance with an embodiment. A dilator system 100 may comprise more than one core 102 each defining different core curves 118 that a user may select during a procedure, in accordance with an embodiment. A variety of cores 102 may be offered as a kit to provide multiple options to a user when encountering different anatomical bends within a blood vessel. The number and type of cores 102 utilized may depend on the individual patient's anatomy and the path taken within the body. Further, a dilator system 100 may comprise a combination of the above described cores 102, in accordance with embodiments.

The dimension of the core curve 118 of the core 102 may be altered when positioned within a dilator lumen 106 where the inherent stiffness of the dilator 103 is imposed on the core 102. The dimension of the core curve 118 of the core distal end 109 outside of the dilator lumen 106 as compared with dimension of the core curve 118 of the core 102 when contained within the dilator lumen 106 may be different and a user may compensate for this difference when choosing a core 102 having a core curve 118 for a particular bend in a blood vessel.

Catheter Introducer System

Figure 5:
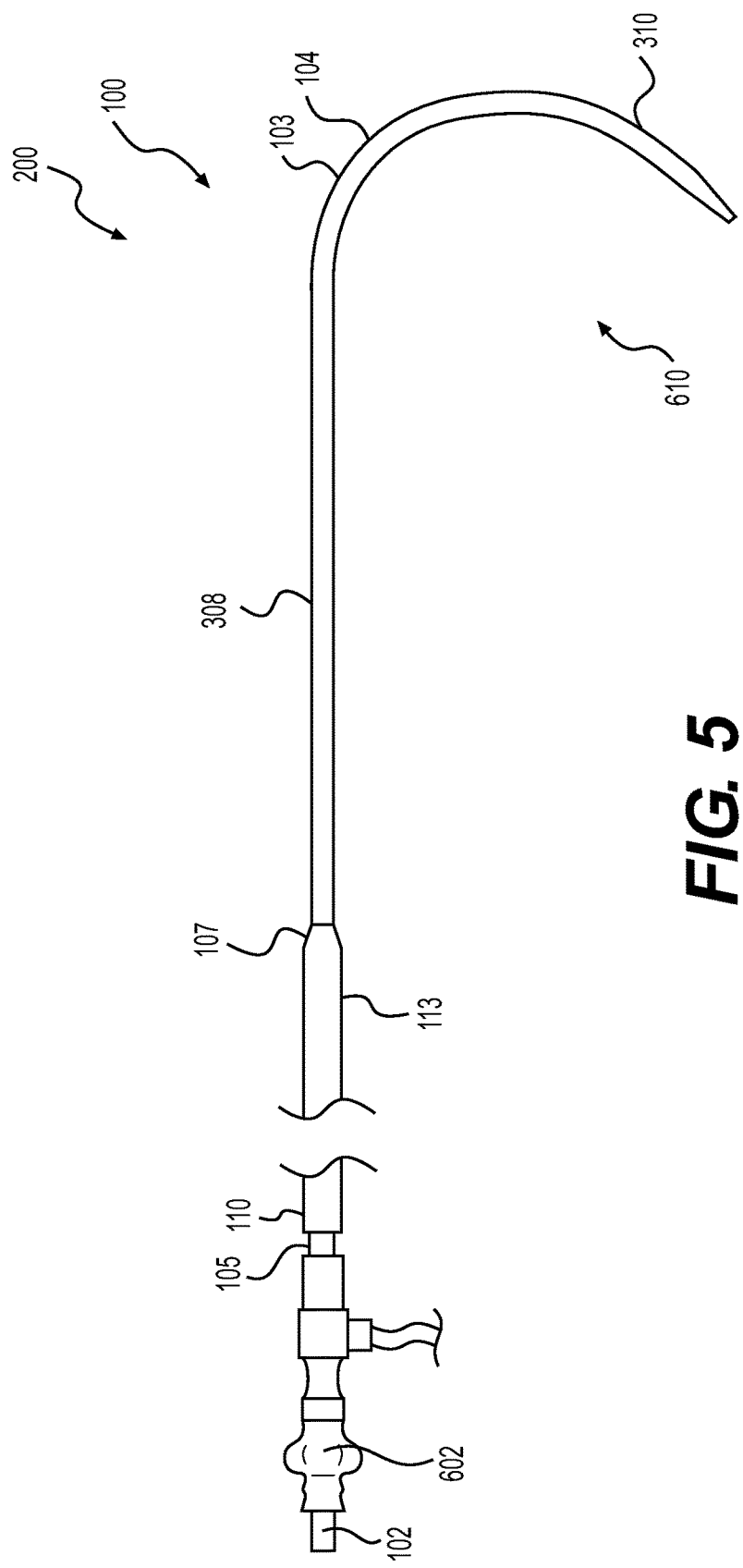
FIG. 5 is a side view of a catheter introducer system, in accordance with an embodiment.

Referring again to FIG. 1, a catheter introducer system 200 comprising the dilator system 100 and a sheath 113 is discussed below. FIG. 5 is a side view of the catheter introducer system 200 as assembled, in accordance with an embodiment. The sheath 113 is operable to be placed within the blood vessel with the assistance of the dilator system 100. After the sheath 113 is properly placed within the blood vessel, the dilator system 100 is withdrawn from the sheath 113, with the sheath 113 remaining to provide a conduit for introducing a catheter into the blood vessel.

The sheath 113 is an elongated tubular member having a sheath proximal end 110 and a sheath distal end 107 opposite from the sheath proximal end 110. The sheath 113 further includes a sheath lumen 116 extending from the sheath proximal end 110 to the sheath distal end 107, therethrough. The sheath lumen 116 defines a diameter that is operable to slidingly receive the dilator 103 therein and to allow the sheath 113 to advance over the dilator 103. In accordance with an embodiment, the sheath 113 has a diameter of about 1 mm to about 10 mm, or about 4 mm to about 8 mm.

The dilator 103 may be used to dilate (enlarge) narrow portions of the blood vessel in order for a larger diameter sheath 113 to advance therethrough. Although the dilator system 100 may be used to enlarge a narrowed blood vessel, the dilator system 100 may also, or alternatively, be used to assist the advancement of a sheath 113 into the blood vessel. The dilator 103 may also be used simply as a guide for advancing the sheath 113 through the blood vessel without necessarily enlarging the blood vessel. In accordance with an embodiment, after the dilator 103 is advanced within the blood vessel, the sheath distal end 107 is advanced over the dilator proximal end 105 and advanced on the dilator 103 toward the dilator distal end 104, with the dilator 103 guiding the sheath 113. In accordance with another embodiment, the sheath distal end 107 is advanced over the dilator proximal end 105 and advanced over at least a portion of the dilator distal end 104 prior to the dilator 103 entering the blood vessel. In other words, the sheath 113 may be at least partially advanced over the dilator 103 prior to use, as shown in FIG. 5.

To assist the sheath distal end 107 to track the dilator 103, a core 102 is advanced into the dilator lumen 106 at the dilator proximal end 105 and is advanced to the dilator distal end 104 at that location where the sheath 113 may tend to mistrack. The core distal end 109 is provided with a predetermined core curve 118 that is operable to impart a curve to the dilator distal end 104 and to provide support thereto. The combination of the dilator 103 supported by the core 102 provides sufficient stiffness at the core curve 118 suitable to support and guide the sheath distal end 107 through the bend of the blood vessel and to substantially prevent the dilator distal end 104 from straightening out under the influence of the sheath 113 advancing thereover.

The relative stiffness of the core 102 within the dilator distal end 104, which is greater than the stiffness of the sheath 133, tends to urge the sheath distal end 107 to track about the curve imposed by the core distal end 109 when the sheath 113 is advanced over the core curve 118. The stiffness of the core 102 is selected so as to be more stiff than the dilator 103, such that the core 102 is capable of supporting the dilator distal end 104 in a particular curved configuration sufficient to guide either the dilator distal end 104 into or through the bend or to guide the sheath distal end 107 over the core curve 118 and through the bend, or both. The stiffness of the core 102 and dilator 103 combined is operable so as to be more stiff than the sheath 113, in accordance with an embodiment.

The core curve 118 of the core distal end 109 is as least partially suppressed, that is, the core distal end 109 is at least partially straightened, while moving through the sheath 113. The core curve 118 of the core distal end 109 is substantially expressed once the core distal end 109 is outside of the confines of the sheath 113. The sheath 113 must not be so stiff as to be unwilling to track over the imparted curve of the dilator distal end 104 as supported by the core 102.

In accordance with an embodiment, once the core curve 118 of the core distal end 109 within the dilator distal end 104 is placed within the bend of the blood vessel, the core 102 may be held in place while the dilator 103 and sheath 113 are advanced over the core 102 and through the bend with the core 102 guiding the dilator distal end 104 and sheath distal end 107 through the bend.

In another embodiment, once the dilator distal end 104 is advanced over the core curve 118 of the core 102 and beyond the bend, with the core curve 118 of the core distal end 109 remaining within the bend of the blood vessel, the dilator 103 and the core 102 are held in place while the sheath 113 is advanced over the dilator 103 and through the bend.

The sheath 113 has a relatively thin wall thickness and comprises a stiffness that is sufficiently low to allow the sheath 113 to track though the blood vessel 203. Referring to FIGS. 3, 4A and 4B, the sheath 113 includes a sheath distal tip 306 that tapers to an interface with the dilator 103 so as to provide, among other things, a smooth transition between the dilator 103 and the sheath 113. Depending on the stiffness of the sheath 113, as the sheath distal end 107 traverses over the curve defined by the dilator 103 as supported by the core curve 118 of the core 102, the sheath distal tip 306 may deform from a circular shape to an oval shape, referred to as ovalization. Ovalization may present an enlarged gap between the dilator 103 and the sheath 113 and may present an edge of the sheath distal end 107 that may damage the blood vessel as it is advanced along the curve.

In accordance with an embodiment, the sheath distal tip 302 has a stiffness that is greater than the stiffness of the remainder of the sheath distal end 107. The stiffness of the sheath distal tip 302 can be an inherent property of the material that the sheath distal tip 302 comprises or affected by an element coupled to the sheath distal tip 302, such as, but not limited to, a stiffening band. The sheath distal tip 302 defines a length that is sufficiently short so as to not to significantly prevent the sheath distal tip 302 from traversing the curve but is sufficiently long so as to support the sheath distal tip 302 to prevent significant ovalization. The length of increased stiffness of the sheath distal tip 306 may define a length of about 1 mm to about 10 mm in length, in accordance with an embodiment.

FIG. 4B is an enlarged cross-sectional view of the sheath distal end 107 of the embodiment of FIG. 4A. The sheath distal end 107 includes a stiffening band 304 operable to impart a stiffness at the sheath distal end 107 that is greater than the stiffness proximate to the stiffening band. The stiffening band 304 is operable to substantially prevent ovalization of the sheath distal tip 302 when the sheath distal tip 302 traverses a bend in the blood vessel. Any gap that may form between the dilator 103 and the sheath distal end 107 when they are in a curved position may be substantially prevented or may be less than about 0.5 mm when the sheath distal tip 302 has a predetermined stiffness that is greater than the stiffness of the remainder of the sheath distal end 107. The sheath distal tip 306 and the stiffening band 304 may define a length of increased stiffness of about 1 to about 10 mm in length, in accordance with an embodiment. The sheath distal tip 306 may be tapered to provide a smooth transition between the sheath 113 and the dilator 103.

The sheath 113 may comprise one or more radiopaque markers 312 to assist visualization under x-ray imaging.

Figure 6:
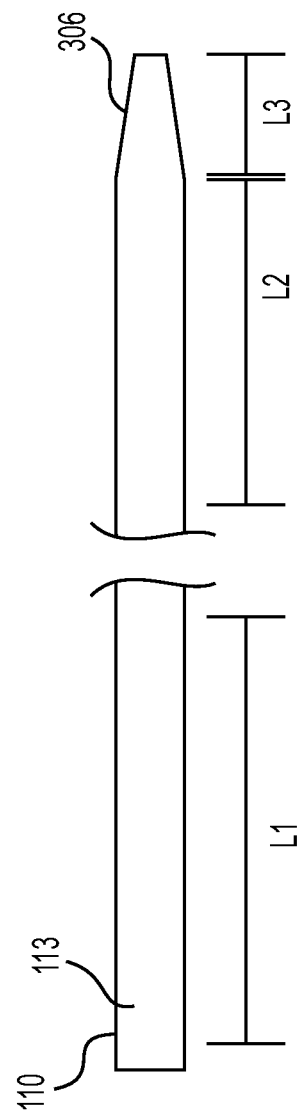
FIG. 6 is a side view of a sheath, in accordance with an embodiment.

FIG. 6 is a side view of a sheath 113 with regions having different stiffness, in accordance with embodiments. The sheath 113 may have two or more regions of varied or differing stiffness. In accordance with an embodiment, the sheath proximal end 110 may define a first length L1 comprising a higher durometer material or characteristic operable to allow a user to more easily manipulate the sheath 113 from the sheath proximal end 110 during advancement through the blood vessel. One or more central portions 115 of the sheath 113 may define a second length L2 comprising a material or material characteristic with a stiffness less than the sheath proximal end 110, and thus being more flexible than the sheath proximal end 110. For example, the durometer at the first length L1 may be about 30 to about 45 and the durometer at the second length L2 may be about 15 to about 30 as measured with a Shore D standard. The first length L1 and the second length L2 may be about 10 cm to about 100 cm in length.

The benefit of the central portion 115 being more flexible than the sheath proximal end 110 allows the central portion 115 to more readily take the form of the curve shape provided by the core 102 and dilator 103. As previously described, in accordance with embodiments, the sheath distal tip 306 at third length L3 comprises a higher durometer or stiffness than the adjacent central portion 115 to substantially prevent ovalization. For example, the sheath distal tip 306 may have a durometer of, such as, but not limited to, about 60 to about 90 as measured with a Shore D standard.

FIG. 3 is a side view of a distal region 325 of the catheter introducer system 200 substantially the same as the embodiment of FIG. 5, in accordance with an embodiment. The dilator 103 and sheath 113 are assembled such that the dilator distal end 104 extends a predetermined distance from the sheath distal end 107, defining an elongated dilator distal region 308. The elongated dilator distal region 308 has a length suitable to allow the core distal end 109 to impart the curve thereon thereon when inserted therein. Without the elongated dilator distal region 308, the dilator 103 may be restricted from defining a curve by the proximity of the relatively stiff sheath 113 to the dilator distal end 104. There are varying ranges of lengths of the elongated dilator distal region 308 suitable for various embodiments, including a length of about 5 cm to about 35 cm, about 10 cm to about 30 cm, about 12 cm to about 17 cm or about 8 cm to about 12 cm.

The length of the elongated dilator distal region 308 can be adjusted, manipulated and held temporarily static by a user during a procedure to position the dilator 103 and/or sheath 113 in combination with a core 102. As will be discussed below, the dilator 103 and the sheath 113 may be coupled together to temporarily prevent movement of the dilator 103 within the sheath 113, such as when the catheter introducer system 200 is positioned in the blood vessel as an assembly.

FIG. 4A is a cross-sectional view of a distal region 325 of a catheter introducer system 200, in accordance with an embodiment of FIGS. 3 and 5. The core distal end 109 of the core 102 is positioned at least partially within the dilator lumen 106 of the dilator 103 at the dilator distal end 104. At least a portion of the dilator distal end 104 is positioned within the sheath lumen 116 of the sheath 113 at the sheath distal end 107. The core 102 may be advanced within the dilator lumen 106 to a substantially distal position, such as in proximity to the dilator distal tip 310 but not extending therefrom, as shown in FIGS. 4A, 4C.

Referring again to FIG. 6, the catheter introducer system 600 further comprises a hub 602 coupled to the dilator proximal end 105. The hub 602 may be used as a handle for guiding the catheter introducer system 600. The hub 602 may be operable to couple the dilator 103 to one or both of the sheath 113 and the core 102. As shown, the sheath 113 is distal from the hub 602 and may be slidably advanced over the dilator 103 towards the dilator distal end 104.

In another embodiment, the sheath proximal end 110 may be coupled to the hub 602 such that the dilator 103 and the sheath 113 may be advanced in the blood vessel without relative movement between the dilator 103 and the sheath 113. Coupling the sheath 113 to the dilator 103 facilitates simultaneous advancement of the dilator 103 and the sheath 113 over a core 102 that may be held stationary, for example.

In accordance with an embodiment, the core 102 may be coupled to the dilator 103 so as to retain the position of the core 102 within the dilator 103 as the sheath 113 is advanced thereover. Coupling may be temporary and can be affected by the use of a threaded, snap or rotary coupler, for example, as is known in the art. Coupling the components at the hub 602 can provide more user control and assembly stability while advancing one or more of the components or the entire system through the blood vessel, for example.

In another embodiment, the core 102 may be provided with a keyed element for cooperative engagement with a keyed feature on the dilator 103 operable to facilitate torsional response or torque when utilized by a user. Such cooperative keyed features may include, such as, but not limited to, a complimentary male/female ridge/groove feature to improve engagement and increase stability between the core 102 and dilator 103.

Guidewire Systems

A guidewire 112 may be used to initially traverse the blood vessel, in accordance with embodiments of the dilator guidewire system 400 and the catheter introducer guidewire system 300. The guidewire distal end 114 of the guidewire 112 is advanced through the blood vessel to a desired location. A relatively floppy guidewire distal end 114 provides the ability for the guidewire 112 to be advanced through complex bends of a blood vessel. The dilator distal end 104 of the dilator 103 may be advanced over the guidewire proximal end 117 and advanced through the blood vessel guided by the guidewire 112. When a core 102 is used, the core distal end 109 may be advanced onto the guidewire proximal end 117 with the core lumen 111 receiving the guidewire 112 therein. As the core 102 is advanced over the guidewire 112, the core 102 is also received by and advanced through the dilator lumen 106.

During use, the guidewire 112 may be withdrawn and inserted or reinserted into the core lumen 111 or the dilator lumen 106 if the core 102 is not being used. Also the core 102 may be withdrawn and inserted or reinserted into the dilator lumen 106 during use.

Figure 7A:
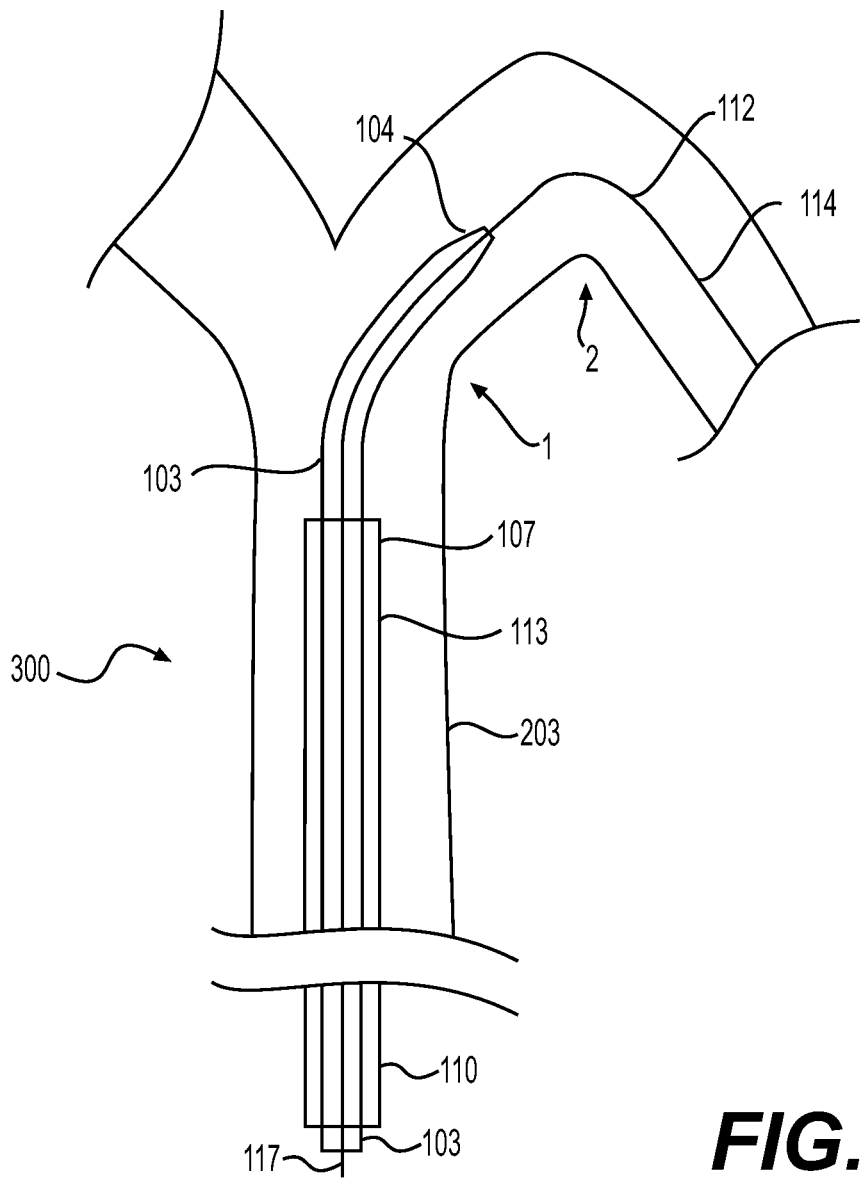
FIG. 7A-7F are cross-sectional views of a catheter introducer system in a blood vessel, in accordance with an embodiment.

The following is an embodiment of a method of use of the catheter introducer guidewire system 300 of FIGS. 1 and 5, by way of example, that will also at least partially apply to the embodiments of methods of use of the dilator system 100, the catheter introducer system 200, and dilator guidewire system 400. FIG. 7A is a cross-sectional view of a blood vessel 203 including a first bend 1 and a second bend 2. In this view, the guidewire distal end 114 has been advanced through the first bend 1 and the second bend 2 with the guidewire proximal end 117 accessible outside of the blood vessel 203. The dilator distal end 104 has been advanced over the guidewire 112 beyond the first bend 1 guided by the guidewire 112. The dilator 103 is able to substantially track on the guidewire 112 due to the relative flexibility of the dilator 103. The sheath distal end 107 is advanced over the dilator proximal end 105 and advanced over the dilator 103 such that the sheath distal end 107 is before and adjacent to the first bend 1.

Figure 7B:
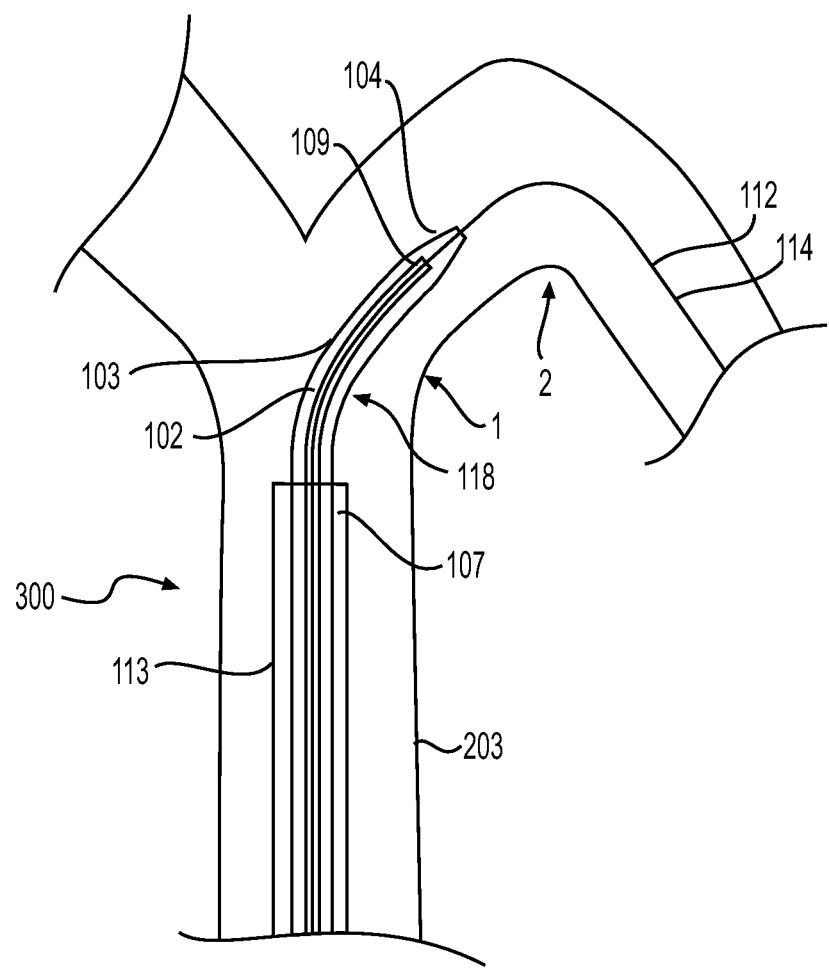

FIG. 7B is a cross-sectional view of the blood vessel 203 where a core distal end 109 of the core 102 has been advanced within the dilator lumen 106 and over the guidewire 112 such that the core curve 118 of the core distal end 109 is within the first bend 1. The core distal end 109 thus provides support to the dilator distal end 104 such that the sheath distal end 107 may track over the dilator 103 within the first bend 1. The core 102 remains within the dilator lumen 106 and the dilator distal end 104 extends from the sheath distal end 107.

Figure 7C:
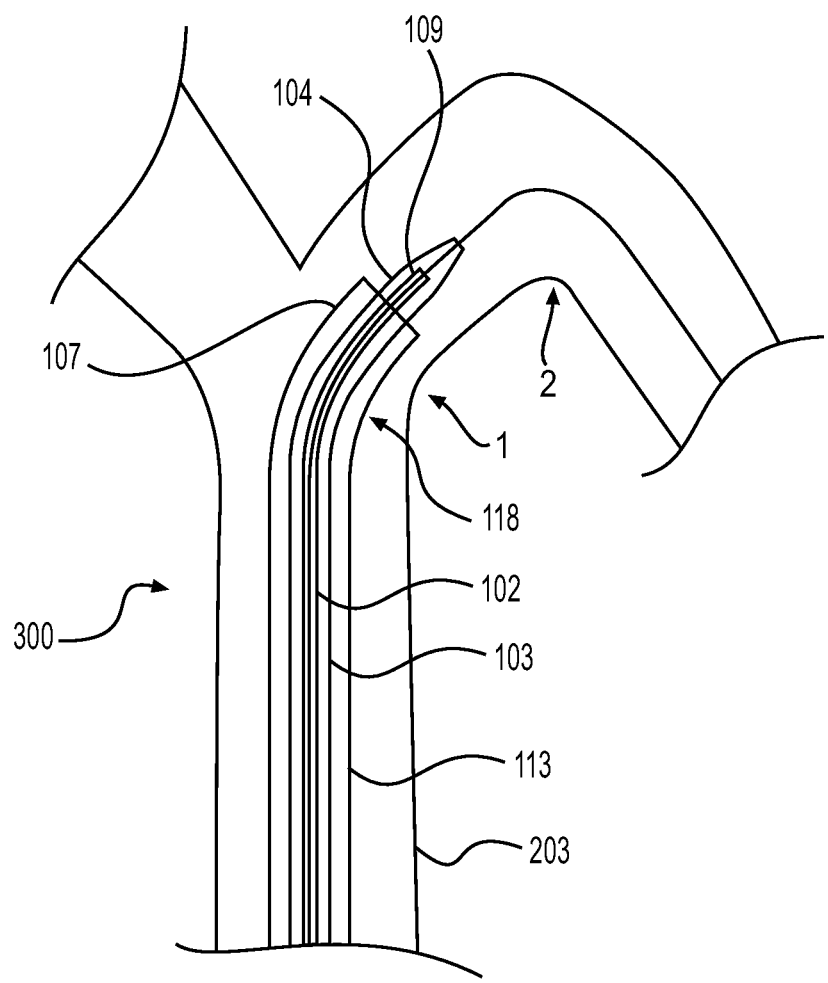

FIG. 7C is a cross-sectional view of the blood vessel 203 where the sheath distal end 107 has been advanced over a portion of the dilator distal end 104, over the core curve 118 and beyond the first bend 1 but before the second bend 2. The second bend 2 is too tortuous for the dilator distal end 104 to track over the guidewire 112 and through the second bend 2 without requiring the support of a core 102.

Figure 7D:
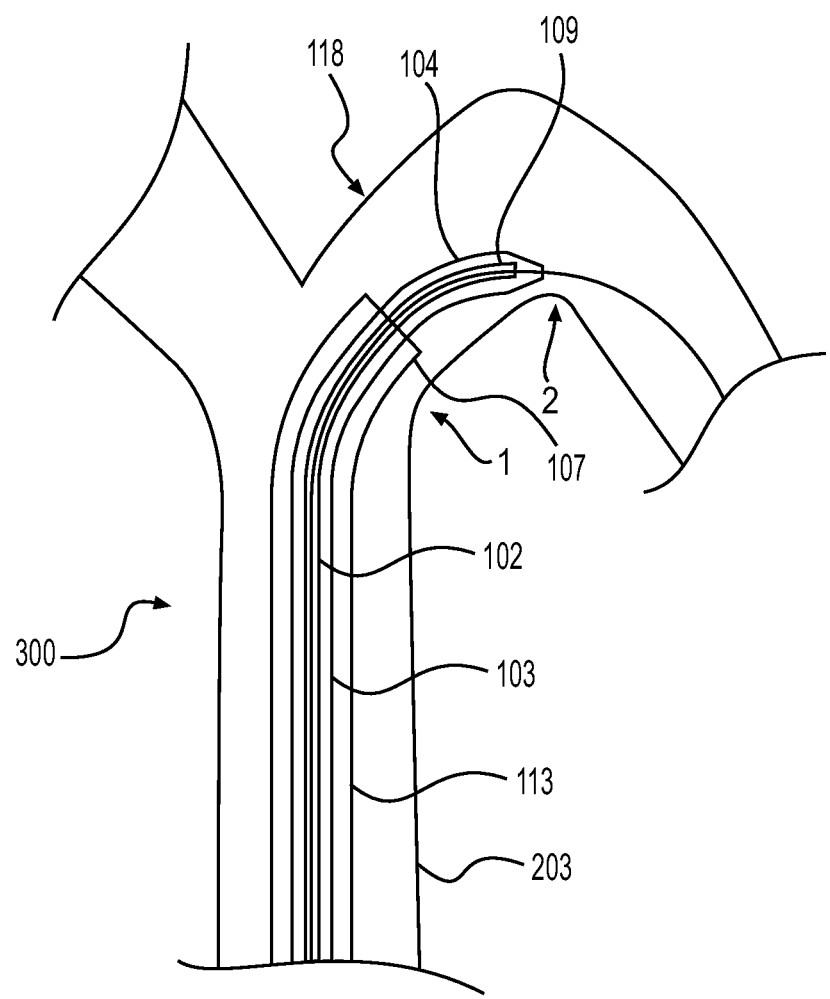

FIG. 7D is a cross-sectional view of the blood vessel 203 where the dilator distal end 104 has been advanced a bit further through the blood vessel 203 and just before the second bend 2. Either the same core 102 or a different core 102 having a different core curve 118 has been advanced through the dilator 103 to the dilator distal end 104. The core distal end 109 defines a cure curve 118 that assists to curve the dilator distal end 104 to direct the dilator distal end 104 towards the second bend 2. As the dilator distal end 104 is advanced further into and through the second bend 2, the core distal end 109 may be advanced with or within the dilator distal end 104 to further direct the dilator distal end 104 through the second bend 2, until the core curve 118 is placed within the second bend 2. The core distal end 109 remains in the dilator lumen 106 while the dilator distal end 104 traverses the second bend 2. If the core 102 were to extend from the dilator distal end 104, the core distal end 109 may damage the blood vessel 203 due to it being a relatively stiff member.

Figure 7E:
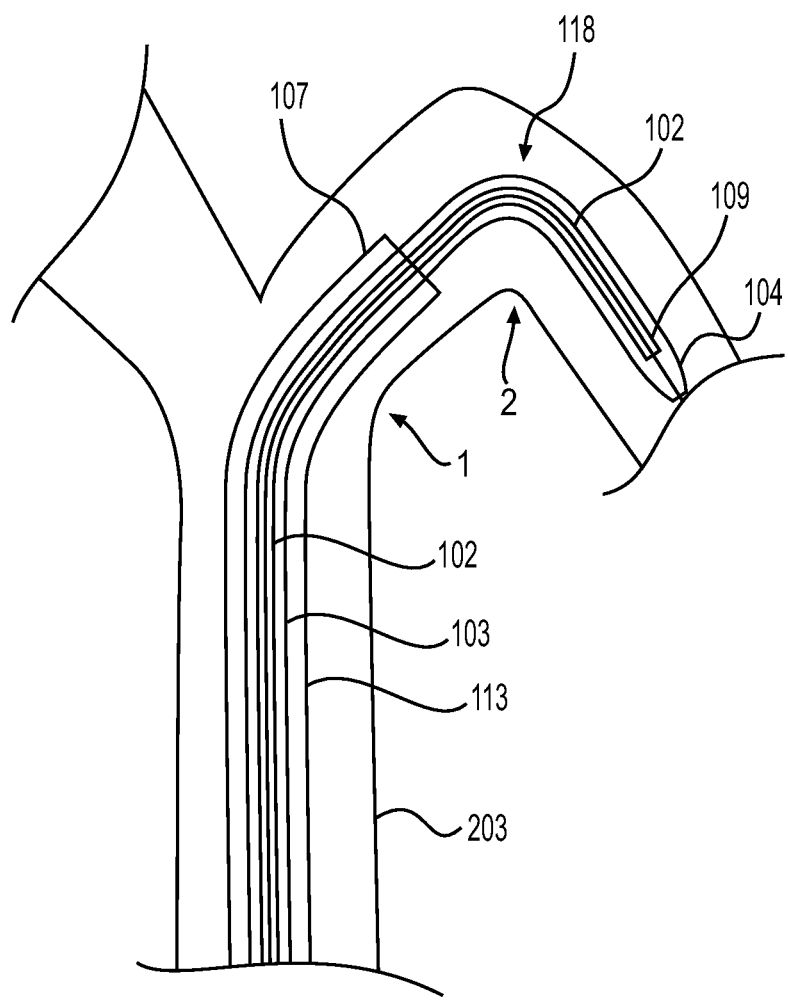

FIG. 7E is a cross-sectional view of the blood vessel 203 where the dilator distal end 104 has passed through the second bend 2. Either the same core 102 or a different core 102 having a different core curve 118 has been advanced through the dilator 103 to the dilator distal end 104 to the second bend 2 such that the core curve 118 defined by the core distal end 109 is within the second bend 2. The core curve 118 thus provides support to the dilator distal end 104 such that the sheath distal end 107 may track over the dilator 103 within the second bend 2.

Figure 7F:
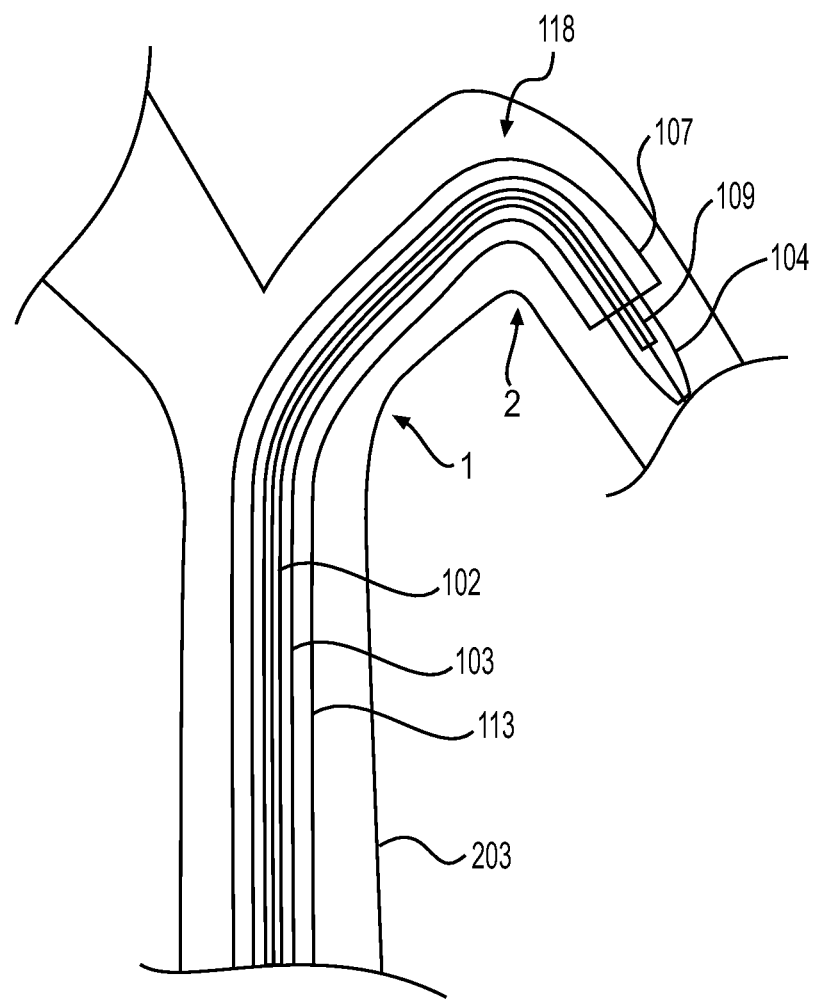

FIG. 7F is a cross-sectional view of the blood vessel 203 where the sheath distal end 107 has been advanced over the dilator distal end 104 beyond the second bend 2.

Figure 8:
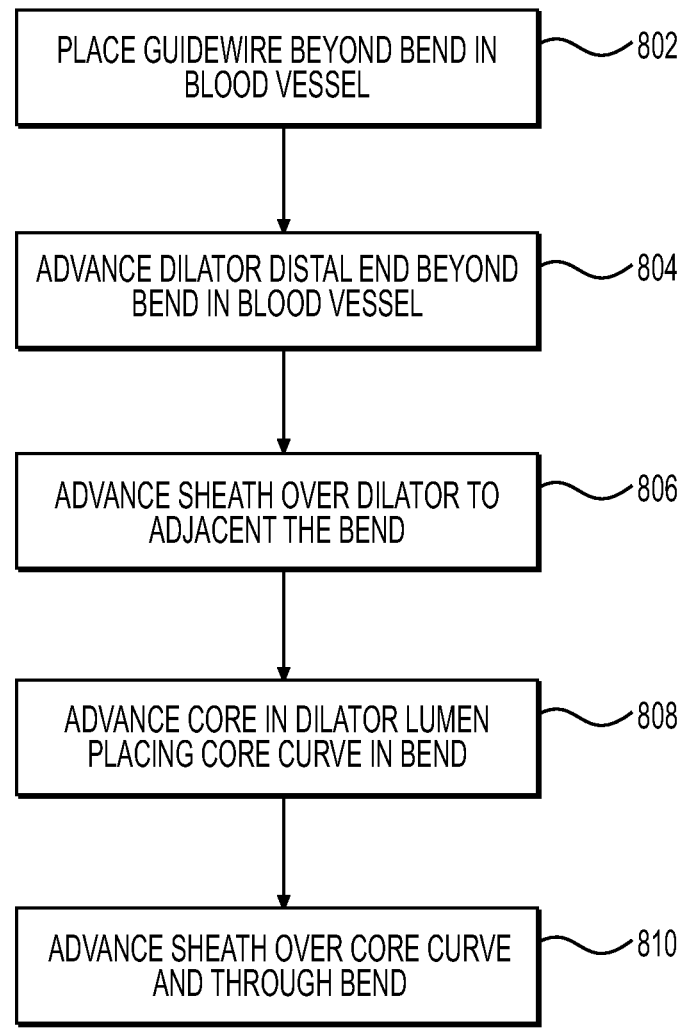
FIG. 8 is a block flow diagram of a method of positioning a catheter introducer system, in accordance with an embodiment.

FIG. 8 is a block flow diagram 800 of a method of positioning a catheter introducer system in a blood vessel, in accordance with an embodiment. A guidewire is advanced through a blood vessel and placed beyond a bend in the blood vessel 802. A dilator distal end is advanced onto a proximal end of the guidewire and into the blood vessel and positioned beyond the bend guided by the guidewire 804. A sheath is advanced onto a proximal end of a dilator and advanced to adjacent the bend 806. A core defining a core curve is advanced through the lumen of the dilator and over the guidewire placing the core curve in the bend 808. Advancing the sheath and the dilator over the core while retaining the position of the core curve in the bend 810.

Figure 9:
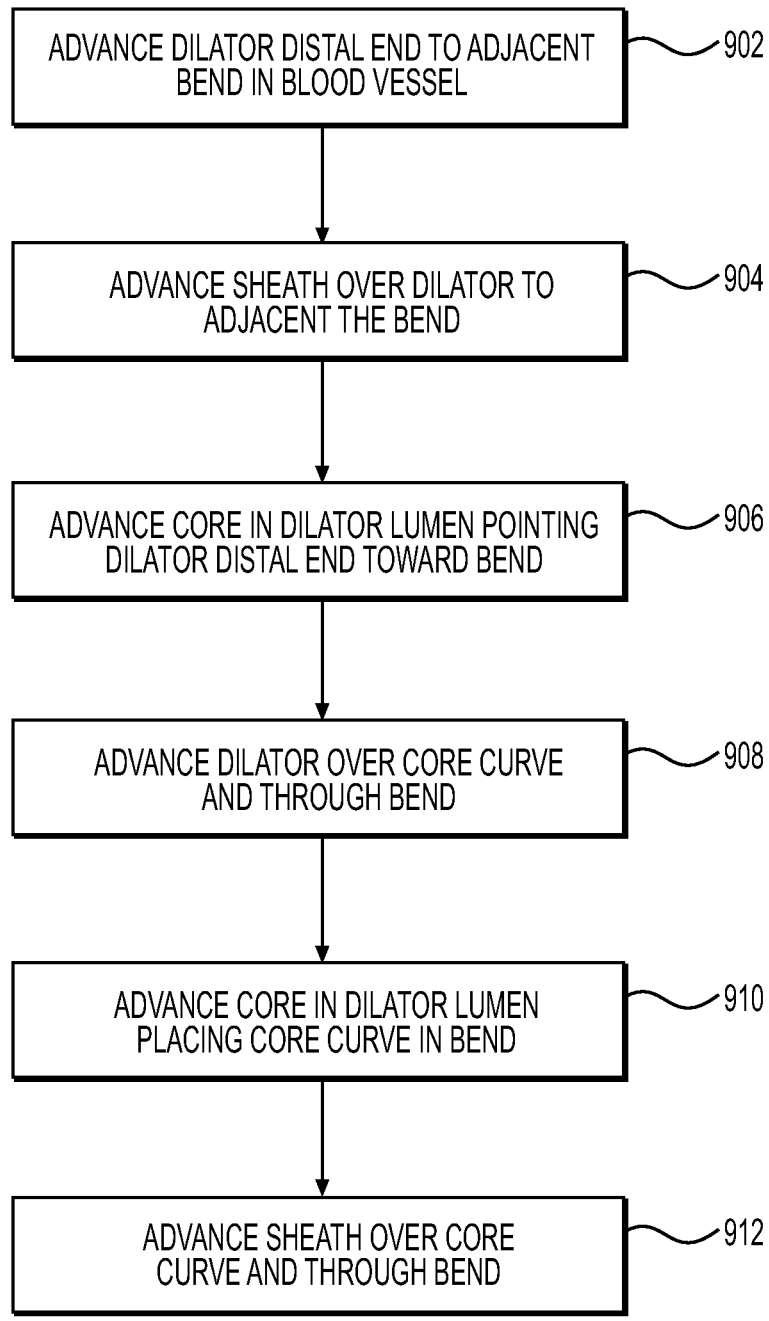
FIG. 9 is a block flow diagram of another method of positioning a catheter introducer system, in accordance with an embodiment.

FIG. 9 is a block flow diagram 900 of another method of positioning a catheter introducer system in a blood vessel, in accordance with an embodiment. A dilator is advanced through a blood vessel with a proximal end of a dilator advanced to adjacent a bend in the blood vessel 902. A sheath is advanced onto a proximal end of a dilator and advanced to adjacent the dilator distal end 904. A core defining a core curve is advanced through the lumen of the dilator and positioned in the dilator distal end causing the dilator distal end to substantially take the shape of the core curve in the direction of the bend 906. Advancing the dilator over the core and through and beyond the bend 908. Advancing the core curve through the dilator placing the core curve in the bend 910. Advancing the sheath distal end and the dilator over the core and beyond the bend while retaining the position of the core curve in the bend 912.

Example

A dilator was produced by extruding an elongated tubular member comprising 50% low-density polyethylene (LDPE) (Westlake Chemical, Houston, Tex.) and 50% Santoprene 281-73MED (ExxonMobil Chemical, Houston, Tex.). The elongated tubular member had an outer diameter of 6.66 mm and an inner diameter of 2.87 mm. A molded tapered tip having the same composition was produced and thermally bonded to an end of the elongated tubular member. The approximate length of the tapered tip was 50 mm. The tapered tip had a diameter of approximately 1.2 mm at a distal end. The total length of the resulting dilator was 1.14 m. A hub was bonded to the proximal end of the dilator. A hydrophilic coating was applied to the outer surface of the dilator.

A number of cores were produced from tubing comprising the material Grilamid L25 (EMS-Grivory, Sumter, S.C.). The tubing had an inner diameter of 1.27 mm and an outer diameter of 2.67 mm. The distal end of the cores were held in a curved configuration using tooling and processed in an oven at 150° C. for 30 min. The core was cooled to room temperature and removed from the tooling, substantially retaining the heat-set shape. One core had a 50 mm radius curve at the distal end. The total length of core was 1.22 m.

A sheath was produced having a higher durometer distal tip comprising PEBAX 7233 SA01 MED (Arkema, King of Prussia, Pa.) compared with the remainder of the sheath.

The dilator, cores and sheath produced above exhibited the properties as described herein.

It will be apparent to those skilled in the art that various modifications and variations can be made in the present embodiments without departing from the spirit or scope of the embodiments. Thus, it is intended that the present embodiments cover the modifications and variations of this invention provided they come within the scope of the appended claims and their equivalents.

What is claimed is:

1. A catheter introducer system for accessing a blood vessel comprising:
   a dilator, the dilator being an elongated tubular member having a dilator proximal end and a dilator distal end opposite from the dilator proximal end, the dilator distal end including a dilator distal tip, the dilator further including a dilator lumen extending from the dilator proximal end to the dilator distal end therethrough;
   a core, the core being an elongated member having a core proximal end and a core distal end opposite from the core proximal end, the core distal end including a core curve that defines a curve, the core being operable for positioning in the dilator lumen to impart a curvature to the dilator, the dilator lumen defining a diameter that is operable to slidingly receive the core therein and allow the core to be advanced at least partially within the dilator lumen, the dilator distal tip having a diameter configured to prevent the core from extending beyond the dilator distal tip; and
   a sheath, the sheath being an elongated tubular member including a sheath proximal end and a sheath distal end opposite from the sheath proximal end, the sheath defining a sheath lumen extending from the sheath proximal end to the sheath distal end therethrough, the sheath lumen that is operable to slidingly receive the dilator therein and to allow the sheath to advance over the dilator, wherein the combination of the dilator supported by the core provides sufficient stiffness at the core curve such that the sheath is operable to track over the curvature of the dilator as imparted by the core.

2. The catheter introducer system of claim 1, wherein the core curve is straight.

3. The catheter introducer system of claim 1, wherein the core curve is planar.

4. The catheter introducer system of claim 1, wherein the core curve is three-dimensional.

5. The catheter introducer system of claim 1, further comprising a plurality of cores, each defining different core curves having different radii of curvature.

6. The catheter introducer system of claim 1, wherein the core curve defines any shape suitable for a particular purpose of supporting a dilator to track a bend in a blood vessel.

7. The catheter introducer system of claim 1, wherein the one or more core curves comprise a radius of curvature from straight to about 125 mm.

8. The catheter introducer system of claim 1, wherein the core distal end may be shaped into the curve by a user.

9. The catheter introducer system of claim 1, wherein the core is steerable.

10. The catheter introducer system of claim 1, wherein the core comprises one or more of a thermoplastic and metal.

11. The catheter introducer system of claim 10, wherein the core comprises nylon.

12. The catheter introducer system of claim 10, wherein the core comprises nitinol.

13. The catheter introducer system of claim 1, wherein the core further comprises one or more radiopaque markers.

14. The catheter introducer system of claim 13, wherein the one or more radiopaque markers are positioned at one or more of a core distal end, a core curve, and a core proximal end.

15. The catheter introducer system of claim 1, wherein the dilator lumen comprises a diameter of about 0.5 mm to about 5 mm.

16. The catheter introducer system of claim 1, wherein the dilator distal tip comprises a length of about 1 cm to about 10 cm.

17. The catheter introducer system of claim 16, wherein the dilator distal tip defines a dilator tip lumen having a diameter that is less than a diameter of the core whereby preventing the core from extending beyond the dilator distal tip.

18. The catheter introducer system of claim 1, further comprising means to couple the dilator to the core.

19. The catheter introducer system of claim 18, wherein the means to couple the dilator to the core comprises a hub coupled to the dilator proximal end and operable to couple with the core.

20. The catheter introducer system of claim 1, wherein the core and dilator further comprise cooperative elements operable to facilitate torsional response when utilized by a user.

21. The catheter introducer system of claim 20, wherein the cooperative elements are keyed features.

22. The catheter introducer system of claim 21, wherein the keyed features comprise complimentary male/female ridge/groove features.

23. The catheter introducer system of claim 1, wherein the dilator further comprises a radiopaque marker.

24. The catheter introducer system of claim 1, the dilator comprising a material property with sufficient stiffness to enlarge the blood vessel but not so stiff to damage the blood vessel or not be able to be guided within bends of the blood vessel by the core.

25. The catheter introducer system of claim 1, wherein a stiffness of the core is more stiff than the dilator, such that the core curve is capable of supporting the dilator distal end in a particular curved configuration sufficient to guide the dilator distal end through a bend of the blood vessel.

26. The catheter introducer system of claim 1, wherein the stiffness of the core is more stiff than the dilator, such that the core is capable of supporting the dilator distal end in a particular curved configuration sufficient to guide the sheath distal end over the core curve and through a bend of the blood vessel.

27. The catheter introducer system of claim 1, wherein the sheath distal end includes a sheath distal tip that tapers to an interface with the dilator.

28. The catheter introducer system of claim 27, wherein the sheath distal tip has a stiffness that is greater than the stiffness of a remainder of the sheath distal end.

29. The catheter introducer system of claim 27, wherein the sheath distal tip defines a length that is sufficiently short so as to not to significantly prevent the sheath distal tip from traversing a bend in the blood vessel but is sufficiently long so as to support the sheath distal tip to prevent significant ovalization.

30. The catheter introducer system of claim 29, the sheath distal tip includes a stiffening band operable to impart a stiffness that is greater than a stiffness proximate to the stiffening band, the stiffening band being operable to substantially prevent ovalization of the sheath distal tip when the sheath distal tip traverses a bend in the blood vessel.

31. The catheter introducer system of claim 29, wherein the sheath distal tip defines a length of about 1 mm to about 10 mm in length.

32. The catheter introducer system of claim 31, wherein the sheath tip has a durometer of about 45 to about 90.

33. The catheter introducer system of claim 27, wherein the sheath proximal end defines a first length, wherein the sheath further defines a central portion between the sheath proximal end and the sheath distal end, wherein the central portion defines a second length having a lower stiffness than the first length, and wherein the sheath distal end defines a third length having a higher stiffness than the central portion.

34. The catheter introducer system of claim 33, wherein a durometer of the second length is about 30 to about 50, and a durometer of the third length is about 60-90 as measured with a Shore D standard.

35. The catheter introducer system of claim 33, wherein a durometer at the first length is about 40 to about 60, a durometer at the second length is about 30 to about 50, and a durometer of the third length is about 60 to about 90 as measured with a Shore D standard.

36. The catheter introducer system of claim 35, wherein the first length and the second length are each about 10 cm to about 100 cm in length.

37. The catheter introducer system of claim 27, wherein the sheath has a diameter of about 1 mm to about 10 mm.

38. The catheter introducer system of claim 27, wherein the sheath further comprises one or more radiopaque markers to assist visualization under x-ray imaging.

39. The catheter introducer system of claim 1, wherein the dilator distal end is operable to extend a predetermined distance from the sheath distal end defining an elongated dilator distal region, the elongated dilator distal region having a length suitable to allow the core distal end to impart the curve thereon when inserted therein.

40. The catheter introducer system of claim 39, wherein the elongated dilator distal region has a length of about 5 cm to about 12 cm.

41. The catheter introducer system of claim 1, further comprising means to couple the dilator to one or more of the core and sheath.

42. The catheter introducer system of claim 41, wherein the means to couple the dilator to the one or more of the core and sheath comprises a hub coupled to the dilator proximal end and operable to couple with one or more of the core and sheath.

43. A catheter introducer guidewire system for accessing a blood vessel, comprising:
 a dilator, the dilator being an elongated tubular member having a dilator proximal end and a dilator distal end opposite from the dilator proximal end, the dilator distal end including a dilator distal tip, the dilator further including a dilator lumen extending from the dilator proximal end to the dilator distal end therethrough;
 a core, the core being an elongated member defining a core lumen, the core having a core proximal end and a core distal end opposite from the core proximal end, the core distal end including a core curve that defines a curve, the core being operable for positioning in the dilator lumen to impart a curvature to the dilator, the dilator lumen defining a diameter that is operable to slidingly receive the core therein and allow the core to be advanced at least partially within the dilator lumen, the dilator distal tip having a diameter configured to prevent the core from extending beyond the dilator distal tip;
 a sheath, the sheath being an elongated tubular member including a sheath proximal end and a sheath distal end opposite from the sheath proximal end, the sheath defining a sheath lumen extending from the sheath proximal end to the sheath distal end therethrough, the sheath lumen that is operable to slidingly receive the dilator therein and to allow the sheath to advance over the dilator, wherein the combination of the dilator supported by the core provides sufficient stiffness at the core curve such that the sheath is operable to track over the curvature of the dilator as imparted by the core; and
 a guidewire being an elongated member that is operable for traversing tortuous blood vessels, the core lumen being operable to receive the guidewire therethrough and the core being operable to be advanced over the guidewire.

44. The catheter introducer guidewire system of claim 43, wherein the core curve is straight.

45. The catheter introducer guidewire system of claim 43, wherein the core curve is planar.

46. The catheter introducer guidewire system of claim 43, wherein the core curve is three-dimensional.

47. The catheter introducer guidewire system of claim 43, further comprising a plurality of cores, each defining different core curves having different radii of curvature.

48. The catheter introducer guidewire system of claim 43, wherein the core curve defines any shape suitable for a particular purpose of supporting a dilator to track a bend in a blood vessel.

49. The catheter introducer guidewire system of claim 43, wherein the one or more core curves comprise a radius of curvature from straight to about 125 mm.

50. The catheter introducer guidewire system of claim 43, wherein the core distal end may be shaped into the curve by a user.

51. The catheter introducer guidewire system of claim 43, wherein the core is steerable.

52. The catheter introducer guidewire system of claim 43, wherein the core comprises one or more of a thermoplastic and metal.

53. The catheter introducer guidewire system of claim 52, wherein the core comprises nylon.

54. The catheter introducer guidewire system of claim 52, wherein the core comprises nitinol.

55. The catheter introducer guidewire system of claim 43, wherein the core further comprises one or more radiopaque markers.

56. The catheter introducer guidewire system of claim 55, wherein the one or more radiopaque markers are positioned at one or more of a core distal end, a core curve, and a core proximal end.

57. The catheter introducer guidewire system of claim 43, wherein the dilator lumen comprises a diameter of about 0.5 mm to about 5 mm.

58. The catheter introducer guidewire system of claim 43, wherein the dilator distal tip comprises a length of about 1 cm to about 10 cm.

59. The catheter introducer guidewire system of claim 58, wherein the dilator distal tip defines a dilator tip lumen having a diameter that is less than a diameter of the core whereby preventing the core from extending beyond the dilator distal tip.

60. The catheter introducer guidewire system of claim 43, further comprising means to couple the dilator to the core.

61. The catheter introducer guidewire system of claim 60, wherein the means to couple the dilator to the core comprises a hub coupled to the dilator proximal end and operable to couple with the core.

62. The catheter introducer guidewire system of claim 43, wherein the core and dilator further comprise cooperative elements operable to facilitate torsional response when utilized by a user.

63. The catheter introducer guidewire system of claim 62, wherein the cooperative elements are keyed features.

64. The catheter introducer guidewire system of claim 63, wherein the keyed features comprise complimentary male/female ridge/groove features.

65. The catheter introducer guidewire system of claim 43, the dilator further comprising a radiopaque marker.

66. The catheter introducer guidewire system of claim 43, the dilator comprising a material property with sufficient stiffness to enlarge the blood vessel but not so stiff to damage the blood vessel or not be able to be guided within bends of the blood vessel by the core.

67. The catheter introducer guidewire system of claim 43, wherein a stiffness of the core is more stiff than the dilator, such that the core curve is capable of supporting the dilator distal end in a particular curved configuration sufficient to guide the dilator distal end through a bend of the blood vessel.

68. The catheter introducer guidewire system of claim 43, wherein the stiffness of the core is more stiff than the dilator, such that the core is capable of supporting the dilator distal end in a particular curved configuration sufficient to guide the sheath distal end over the core curve and through a bend of the blood vessel.

69. The catheter introducer guidewire system of claim 43, wherein the sheath distal end includes a sheath distal tip that tapers to an interface with the dilator.

70. The catheter introducer guidewire system of claim 69, wherein the sheath distal tip has a stiffness that is greater than the stiffness of a remainder of the sheath distal end.

71. The catheter introducer guidewire system of claim 70, wherein the sheath distal tip defines a length of about 1 mm to about 10 mm in length.

72. The catheter introducer guidewire system of claim 71, wherein the sheath tip has a durometer of about 45 to about 90.

73. The catheter introducer guidewire system of claim 69, wherein the sheath distal tip defines a length that is sufficiently short so as to not to significantly prevent the sheath distal tip from traversing a bend in the blood vessel but is sufficiently long so as to support the sheath distal tip to prevent significant ovalization.

74. The catheter introducer guidewire system of claim 73, the sheath distal tip includes a stiffening band operable to impart a stiffness that is greater than a stiffness proximate to the stiffening band, the stiffening band being operable to substantially prevent ovalization of the sheath distal tip when the sheath distal tip traverses a bend in the blood vessel.

75. The catheter introducer guidewire system of claim 69, wherein the sheath proximal end defines a first length, wherein the sheath further defines a central portion between the sheath proximal end and the sheath distal end, wherein the central portion defines a second length having a lower stiffness than the first length, and wherein the sheath distal end defines a third length having a higher stiffness than the central portion.

76. The catheter introducer guidewire system of claim 75, wherein a durometer of the second length is about 30 to about 50, and a durometer of the third length is about 60-90 as measured with a Shore D standard.

77. The catheter introducer guidewire system of claim 75, wherein a durometer at the first length is about 40 to about 60, a durometer at the second length is about 30 to about 50, and a durometer of the third length is about 60 to about 90 as measured with a Shore D standard.

78. The catheter introducer guidewire system of claim 77, wherein the first length and the second length are each about 10 cm to about 100 cm in length.

79. The catheter introducer guidewire system of claim 69, wherein the sheath has a diameter of about 1 mm to about 10 mm.

80. The catheter introducer guidewire system of claim 69, wherein the sheath further comprises one or more radiopaque markers to assist visualization under x-ray imaging.

81. The catheter introducer guidewire system of claim 43, wherein the dilator distal end is operable to extend a predetermined distance from the sheath distal end defining an elongated dilator distal region, the elongated dilator distal region having a length suitable to allow the core distal end to impart the curve thereon when inserted therein.

82. The catheter introducer guidewire system of claim 81, wherein the elongated dilator distal region has a length of about 5 cm to about 35 cm.

83. The catheter introducer guidewire system of claim 43, further comprising means to couple the dilator to one or more of the core and sheath.

84. The catheter introducer guidewire system of claim 83, wherein the means to couple the dilator to the one or more of the core and sheath comprises a hub coupled to the dilator proximal end and operable to couple with one or more of the core and sheath.

* * * * *